United States Patent [19]

Glogowski et al.

[11] Patent Number: 4,983,315

[45] Date of Patent: Jan. 8, 1991

[54] N,N'-(1-OXO-1,2-ETHANEDIYL)-BIS(ASPARTIC ACID), SALTS AND USE IN DETERGENT COMPOSITIONS

[75] Inventors: Mark W. Glogowski; Frederick A. Hartman; Stephen W. Heinzman; Christopher M. Perkins, all of Cincinnati, Ohio

[73] Assignee: The Procter & Gamble Company, Cincinnati, Ohio

[21] Appl. No.: 392,168

[22] Filed: Aug. 10, 1989

[51] Int. Cl.$^5$ .................. C01B 15/037; C02F 5/12; C11D 3/33; C07C 229/26
[52] U.S. Cl. .................................. 252/102; 210/638; 210/749; 210/912; 252/117; 252/180; 252/186.25; 252/186.31; 252/527; 252/546; 252/DIG. 11; 252/186.29; 424/62
[58] Field of Search ................. 562/565; 210/638, 749, 210/912; 252/102, 117, 180, 186.25, 186.29, 186.31, 527, 546, DIG. 11

[56] References Cited

U.S. PATENT DOCUMENTS

| | | | |
|---|---|---|---|
| 2,264,103 | 11/1941 | Tucker | 252/132 |
| 2,407,645 | 9/1946 | Bersworth | 562/565 |
| 3,077,487 | 2/1963 | Ramsey et al. | 260/429 |
| 3,151,084 | 9/1964 | Schiltz et al. | 252/137 |
| 3,158,635 | 11/1964 | Kezerian et al. | 260/429 |
| 3,635,829 | 1/1972 | Yang | 252/526 |
| 3,637,511 | 1/1972 | Yang | 252/527 |
| 3,692,684 | 9/1972 | Hentschel | 252/174.19 |
| 3,729,432 | 4/1973 | Bruson | 252/545 |
| 3,767,598 | 10/1973 | Bruson | 252/546 |
| 3,859,224 | 1/1975 | Kandler | 252/135 |
| 3,920,564 | 11/1975 | Grecsek | 252/8.75 |
| 3,925,456 | 12/1975 | Plöger | 252/545 |
| 3,954,858 | 5/1976 | Lamberti et al. | 260/535 P |
| 4,021,376 | 5/1977 | Lamberti | 252/542 |
| 4,369,142 | 1/1983 | Moser | 260/502.5 F |
| 4,397,776 | 8/1983 | Ward | 252/527 |
| 4,560,492 | 12/1985 | Curry et al. | 252/110 |
| 4,704,233 | 11/1987 | Hartman et al. | 252/527 |
| 4,826,673 | 5/1989 | Dean | 424/9 |

OTHER PUBLICATIONS

Springer and Kopecka, Chem. Zvesti. 20(6): 414–422 (1966) (CAS abstract 65:11738f) Abstract Only.
Pavelcik and Majer, Chem. Zvesti. 32(1): 37–41 (1978) English—Full Text.
Ingles, Chemistry and Industry, pp. 1492–1493, 1967.
Mathur et al., J. Indian Chem. Sol., May 1973, pp. 353–356.

(List continued on next page.)

Primary Examiner—Dennis Albrecht
Attorney, Agent, or Firm—Lars S. Johnson; Jerry J. Yetter; Richard C. Witte

[57] ABSTRACT

Disclosed are the N,N'-(1-oxo-1,2-ethanediyl)-bisaspartates comprising the moiety

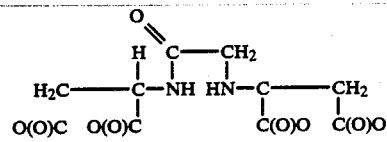

methods for their preparation (including an unexpected preparation from glyoxal bisulfite and aspartic acid in concentrated aqueous alkaline media) and useful compositions containing the same; illustrative are general-purpose sequestrant compositions, chelating agent compositions for transition metals such as iron, manganese and copper, general-purpose laundry detergent compositions and detergent compositions comprising perborate bleach, a bleach activator and, as a bleach stabilizer/performance enhancer, the novel bisaspartates. These unique nonphosphorus compounds are useful at low levels and differ from traditional —N—C—C—N— chelating agents such as ethylenediaminetetraacetates by the presence of one amino- and one amido- functional group which it is believed will provide additional advantages, such as improved biodegradation.

20 Claims, 2 Drawing Sheets

OTHER PUBLICATIONS

Sulfonation and Related Reactions, E. E. Gilbert, 1965, reprinted 1977 with International Standard Book No. ISBN 0-88275-528-5 corrections, John Wiley and Sons; pp. 249-256, 329-330.

Kirk-Othmer, Encyclopaedia of Chemical Technology, 1980 Edition, John Wiley and Sons, vol. 11, pp. 946 and 955.

Reagents for Organic Synthesis, Fieser and Fieser, John Wiley and Sons, 1967; section concerning glyoxal/glyoxal bisulfate.

Adams et al., J. Amer. Chem. Soc. vol. 71, pp. 522-526, 1948.

Neelakantan et al., J. Organic Chemistry, vol. 24, pp. 1943-1948, 1959.

Lacoste et al., J. Amer. Chem. Soc., vol. 77, pp. 5512-5515, 1955.

Neal et al., Inorganic Chemistry, vol. 7, pp. 2405-2412, 1968.

xx = MALEATE IMPURITY
‡‡ = FUMARATE IMPURITY
** = UNIDENTIFIED IMPURITY, POSSIBLY METHANOL x = CARBOXYMETHYLASPARTATE IMPURITY/BYPRODUCT
‡ = L-ASPARTATE IMPURITY/STARTING-MATERIAL

N,N'-(1-OXO-1,2-ETHANEDIYL)-BIS(ASPARTIC ACID), SALTS AND USE IN DETERGENT COMPOSITIONS

TECHNICAL FIELD

The present invention relates to the provision of 1-oxo-1,2-ethanediyl - bisaspartates. The compounds contain an —N—C—C—N— fragment and can be made economically from a symmetrical reagent such as glyoxal bisulfite, yet are unsymmetrical by virtue of one amido- group and one amino- group, and are useful, especially in the sodium salt or acid forms, in a variety of applications, notably domestic or institutional cleaning products including laundry detergents and general-purpose peroxygen bleaches.

BACKGROUND OF THE INVENTION

Uncontrolled metal ions, found ubiquitously as solutions or colloidal suspensions in water, create a great diversity of technical problems, as illustrated by scale or precipitate formation in boilers, difficult cleaning of soils from textile fabrics and hard surfaces and metal-catalyzed decomposition of otherwise useful peroxide, perborate or peracid bleaches. Uncontrolled metal ions, especially those of heavy metals, are often significantly toxic, and in consequence, detoxicants and other pharmaceuticals are needed.

Materials capable of addressing such problems are termed "scale inhibitors", "builders", "water softeners", "sequenstrants", "chelating agents", "bleach stabilizers " and so forth, often depending more on their development history and on arbitrary industry convention than on their prime function or mechanism of action. Certain materials, such as the sodium polyphosphates, are so useful in numerous polyvalent metal-ion control applications that labelling them with only one such term seems to deny their truly multi-functional character. On the other hand, the terms "builder" and "water softener" have come to be conventionally associated with those material which are manufactured in great quantity, mostly for binding calcium or magnesium "hardness" in water, while the terms "sequestrant" and "chelating agent" usually connote high-performance materials, less limited in the range of metal ions they will bind, and capable of controlling numerous metal ions, especially those of the transition metals. "Chelating agents", in particular, tend to form co-ordination complexes with polyvalent metal ions in which there are two or more bonds per metal ion, resulting in one or more strongly bonded "chelate rings". Chelating agents or sequestrants are commonly used in small yet effective amounts in premium cleaning and bleaching products. They enhance cleaning/bleaching performance, very probably due to their typically high binding constants with transition metal ions and consequent ability to tightly bind those ions, even in the presence of a builder.

The use of many widely useful materials based on phosphorus, such as the aforementioned polyphosphates, is increasingly limited by a number of government regulations and certain well-known precipitating builder materials, such as sodium carbonate, are recognized as being much more limited than phosphates in their metal-ion controlling capabilities. Moreover, other builders which act by formation of a water-soluble complex (nitrilotriacetate, NTA, for example, binds both calcium and magnesium rather well in this manner) have been developed but are already subject to regulation; and ion exchange builders, such as zeolite A, bind calcium strongly, but are insoluble.

Today's laundry detergent compositions comprise a wide variety of functional ingredients designed to clean myriad soils and stains from many different types of fabrics and fabric blends. Such functional ingredients include various surfactants and surfactant blends, as well as bleaches and enzymes, and can have various forms. Liquid products are increasingly sought-after. Into such complex formulations, the formulator will usually wish to introduce one or more builders and/or sequestrants so as to achieve superior cleaning. The situation is complicated in that compatibility of the ingredients must be considered, especially in a liquid; moreover the formulator is constrained by various regulations, as noted.

In light of the foregoing, there is a continuing search for chemical compounds which can be used in detergent compositions for broad-brush sequestration of the more commonplace calcium and/or magnesium hardness, as well as (in admixture with conventional builders such as zeolite A) for more specialized purposes, such as iron, copper and maganese sequestration or stabilizing laundry bleaches, e.g., in liquid form. Furthermore, there is a continuing search for metal ion sequestrants, especially those which do not contain phosphorus and are relatively inexpensive.

Accordingly, it is an object of the present invention to provide new compounds, the N,N'-(1-oxo-1,2-ethanediyl)-bis(aspartates), taking a number of forms including the tetraprotic acid, sodium and potassium salts, esters, and stereoisomers thereof. Any N,N'-(1-oxo-1,2-ethanediyl)-bisaspartate compound directly useful as a functional ingredient in detergent compositions, chelating agent compositions, bleaching compositions, builder compositions and other useful compositions provided by the invention is hereinafter identified by its full name or by the acronym "OEDBA". The acronym may be used in abbreviating formulae, e.g., $Na_4$(OEDBA) which is a formula abbreviation for tetrasodium N,N'-(1-oxo-1,2-ethanediyl)-bis(aspartate).

Further objects of the invention include providing methods for making OEDBA, providing a method for sequestering metal ions comprising treating aqueous transition metal-ion containing solutions with OEDBA, and providing chelating agent compositions or sequestrant compositions having an effective amount of OEDBA which are generally useful as a chelating agent, sequestrant or (at higher levels) as water-soluble builder, all without need for isolating the pure compound. It is yet another object herein to provide laundry detergent compositions benefitting from the incorporation of OEDBA as a sequestrant or bleach stabilizer/performance enhancer.

BACKGROUND ART

The use of ethylenediamine-N,N'-disuccinic acid in detergent compositions is described in U.S. Pat. No. 4,704,233, Hartman and Perkins, issued Nov. 3, 1987.

As indicated in U.S. Pat. No. 4,704,233, the use of a number of aminopolycarboxylates as laundry detergent additives is disclosed in the art. For example, the prior art describes laundry detergent compositions which include nitrilotriacetates (NTA), ethylenedediaminetetraacetates (EDTA), diethylenetriaminepentaacetates (DTPA), hydroxyethylethylenediaminetriacetates (HEDTA), and triethylenetetraminehexaacetic acid (TTHA).

U.S. Pat. No. 4,560,492, Curry and Edwards, issued Dec. 24, 1985, discloses laundry detergent compositions, essentially free from phosphate detergency builders, containing an aluminosilicate or organic detergency builder and from about 0.5% to about 10% by weight of HEDTA as a chelant. The list of organic detergency builders disclosed includes aminopolycarboxylates such as NTA, EDTA and DTPA. Examples I and II disclose liquid detergent compositions containing DTPA and HEDTA. Example III discloses a granular detergent composition containing NTA and HEDTA.

U.S. Pat. No. 4,397,776, Ward, issued Aug. 9, 1983, discloses liquid laundry detergent compositions, having a pH between 9 and 13, containing alpha-amine oxide surfactants and from about 0.01% to about 25% by weight of a heavy-metal chelating agent. The chelating agent sequesters heavy-metal ions and thus enhances the stability of the alpha-amine oxides. The preferred chelating agents include aminopolycarboxylates, such as NTA, EDTA, DTPA, and HEDTA.

U.S. Pat. No. 3,920,564, Grecsek, issued Nov. 18, 1975, discloses softener/detergent formulations containing surfactants, quaternary ammonium or diamine fabric softeners, and a builder salt selected from aminopolycarboxylates and/or sodium citrate. Examples of suitable aminopolycarboxylates include NTA, EDTA and HEDTA.

U.S. Pat. No. 3,151,084, Schiltz et al, issued Sept. 29, 1964, discloses alkylbenzenesulfonate-containing detergent compositions in which solubility is said to be improved by the addition of 0.25%–4% of a mixture of EDTA and a solubilizing agent selected from salts of N,N-di(2-hydroxyethyl) glycine, iminodiacetic acid, NTA and HEDTA.

The art also discloses methods of synthesizing EDDS. For example, U.S. Pat. No. 3,158,635, Kezerian and Ramsey, issued Nov. 24, 1964, discloses methods of preparing compounds having the formula:

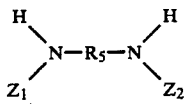

wherein $Z_1$ and $Z_2$ are the same or different bis-adduction residues of unsaturated polycarboxylic acids and salts thereof, and $R_5$ is an alkylene or alkylene-phenylene group. These compounds are taught to be useful for removing rust and oxide coating from metals. If $Z_1$ and $Z_2$ are each —CH(COOH)CH$_2$(COOH) and $R_5$ is —CH$_2$CH$_2$—, then the compound is EDDS. Example 1 discloses a method of synthesizing EDDS from maleic anhydride and ethylenediamine.

Springer and Kopecka, Chem. Zvesti. 20(6): 414–422 (1966) (CAS abstract 65:11738f), discloses a method for synthesizing EDDS and describes the formation of EDDS complexes with several metal ions.

Pavelcik and Majer, Chem. Zvesti. 32(1): 37–41 (1978) (CAS abstract 91(5): 38875f), describe the preparation and properties of the meso and racemate stereoisomer forms of EDDS. The meso and racemate forms were separated via their Cu(II) complexes, with the racemate form being identified from crystallographic data. These compounds are taught to be useful as selective analytical titration agents.

Moser, U.S. Pat. No. 4,369,142, issued Jan. 18, 1983, discloses a novel process for producing the herbicide N-phosphonomethylglycine, comprising reacting aminomethanephosphonic acid with glyoxal, in an aqueous medium, in the presence of sulfur dioxide. Apparently, the product does not contain any —SO$_3$H groups. In contrast, Ingles, Chemistry and Industry, pages 1492–1493, 1967, reports bubbling sulfur dioxide through a suspension of glycine and glyoxal, and assertedly similar reactions of sulfur dioxide with glycine and formaldehyde and diacetyl respectively The product in each instance is said to contain covalently bonded —SO$_3$H.

Other aminocarboxylates known in the literature, and disclosed as being useful in detergent compositions, include carboxymethylaspartate and related derivatives: see U.S. Pat. No. 3,954,858, Lamberti et al, issued May 4, 1976.

SUMMARY OF THE INVENTION

The present invention encompasses the N,N'-(1-oxo-1,2-ethane-diyl)bis-(aspartates), especially the compound N,N'-(1-oxo-1,2-ethanediyl)bis-(aspartic) acid and its derivatives, such as the salts and esters, and compositions containing effective amounts of N,N'-(1-oxo-1,2-ethanediyl)bis-(aspartate). The essential N,N'-(1.oxo-1,2-ethanediyl)bis-(aspartate) moiety is hereinafter given the acronym "OEDBA".

What is an "effective amount" of OEDBA depends on the type of composition and on the desired result. Thus, an "effective amount" can be very low, e.g., about 0.05%–0.95%, preferably 0.1%–0.8%, e.g., when OEDBA is used as a selective chelating agent or bleach performance enhancer, as further illustrated hereinafter. One use of OEDBA in this mode is illustrated by a detergent composition containing, along with the OEDBA at the above-noted level, one or more conventional calcium/ magnesium builders, typically at 5% to about 40% of the detergent composition. When such a detergent composition is placed, with soiled fabrics, in an aqueous laundry bath at the usual level (e.g., about 0.1% to about 2.5%), the conventional builder sequesters or builds calcium and magnesium, and the OEDBA sequesters a variety of other metals, especially transition metals including iron, copper and manganese present in the laundry bath water or on the fabrics as solutions or as colloidal suspensions.

In contrast, if the OEDBA is to be used as a general-purpose builder, the "effective amount" of OEDBA can be significantly higher, e.g., up to 10%, or more, of the detergent composition, and there is no need for a separate calcium/magnesium builder.

Especially at intermediate levels in a laundry composition, e.g., 0.5%–2%, OEDBA can be helpful for removing stains, such as those of grape juice, from soiled fabrics.

More generally, OEDBA can be used in a variety of applications requiring a chelating agent; the "effective amount" of OEDBA can be excess, stoichiometric or substoichiometric in relation to the amount of metal. The amount of metal in a given circumstance can vary widely, for example, depending on the water quality which is very regionally dependent: thus, the formulator should adapt the OEDBA level in the chelating agent compositions in function of the metal concentrations likely to be encountered in the region. Moreover, a colloidal suspension of transition metal oxides can often be treated with substoichiometric amounts of OEDBA with good results, whereas a solution containing freely dissociated transition metal ions will usually require a stoichiometric or near-stoichiometric amount of OEDBA to attain maximum sequestration. Excess OEDBA may be wasteful in terms of sequestration, yet be helpful for other benefits, e.g., stain removal, as noted.

In another specialized application, substoichiometric amounts of OEDBA may also be adequate when, irrespective of sequestration mechanism, the primary objective is to improve cleaning performance of a detergent: for example, OEDBA is effective at preferred levels of about 0.1% to about 0.8% to improve the bleach effectiveness of a laundry detergent containing a conventional bleach activator and perborate bleach and, optionally but preferably, a conventional builder. In such applications, OEDBA is capable of replacing phosphorus-containing chelating agents, EDTA and their mixtures.

The acid and other water-dissociable salts, such as the tetrasodium and tetrapotassium salts, are the preferred forms of OEDBA for use in detergent compositions and in other applications including those wherein the OEDBA acts as a general-purpose, phosphorus-free, builder or chelating agent and those wherein the OEDBA has a more specialized role, such as the above-illustrated activated perborate bleach-containing laundry detergent.

Accordingly, preferred embodiments of the invention include laundry detergent compositions comprising a detersive surfactant and N,N'-(1-oxo-1,2-ethanediyl)-bis-(aspartate) in a water-dissociable form, typically the sodium salts. Detergent compositions comprising a water-dissociable N,N'-(1-oxo-1,2-ethanediyl)-bis-(aspartate) compound and an anionic, nonionic, cationic or zwitterionic detersive surfactant, or mixtures thereof, are particularly useful for laundering fabrics, and are exemplified more fully, hereinafter.

The invention also encompasses bleach compositions, comprising a conventional bleaching agent and OEDBA. Bleach compositions comprising OEDBA and a perborate, persulfate, percarbonate, or peroxide bleaching agent, or mixtures thereof, are particularly useful for fabric cleaning operations.

The invention also encompasses detergency builder compositions, comprising OEDBA and a conventional detergency builder. Builder compositions wherein the conventional builder is a nonphosphorus builder are provided. Especially preferred detergency builder compositions comprise OEDBA and a conventional builder which is a member selected from the group consisting of conventional polycarboxylate builders, zeolite builders, and mixtures thereof.

The invention also encompasses the unexpected discovery of an economically attractive process for preparing OEDBA; comprising reacting an aspartic acid with glyoxal bisulfite under particularly controlled conditions. A second method, comprising reacting glycylaspartate with methyl maleate, is also disclosed. Having more than one synthesis method is of interest for commercial reasons as well as in that the identity of the OEDBA product can convincingly be demonstrated. This is important in view of the fact that the first, more economic, synthesis method would have been expected to result in a totally different product or products.

The invention also encompasses a method of sequestering divalent, trivalent or polyvalent metal cations in aqueous solution, comprising dissolving OEDBA in the cation-containing solution.

A particular advantage of OEDBA resides in that it is a highly weight-efficient chelating agent resulting in perborate bleach-containing laundry detergents which perform their cleaning and bleaching function very well, even when the level of OEDBA in the laundry bath is low (e.g., 20 parts per million). Since, as will be shown hereinafter, OEDBA can be made from D- or L-aspartic acids which are biodegradable materials, and since furthermore, the OEDBA molecule comprises a molecular sub-unit which resembles a peptide, it is predicted that OEDBA will prove biodegradable.

All percentages, ratios and proportions herein are by weight, unless otherwise specified.

DETAILED DESCRIPTION OF THE INVENTION

N,N'-(1-oxo-1,2-ethanediyl)-bis-(aspartate) Compounds: Names and Structure

Figure 1:
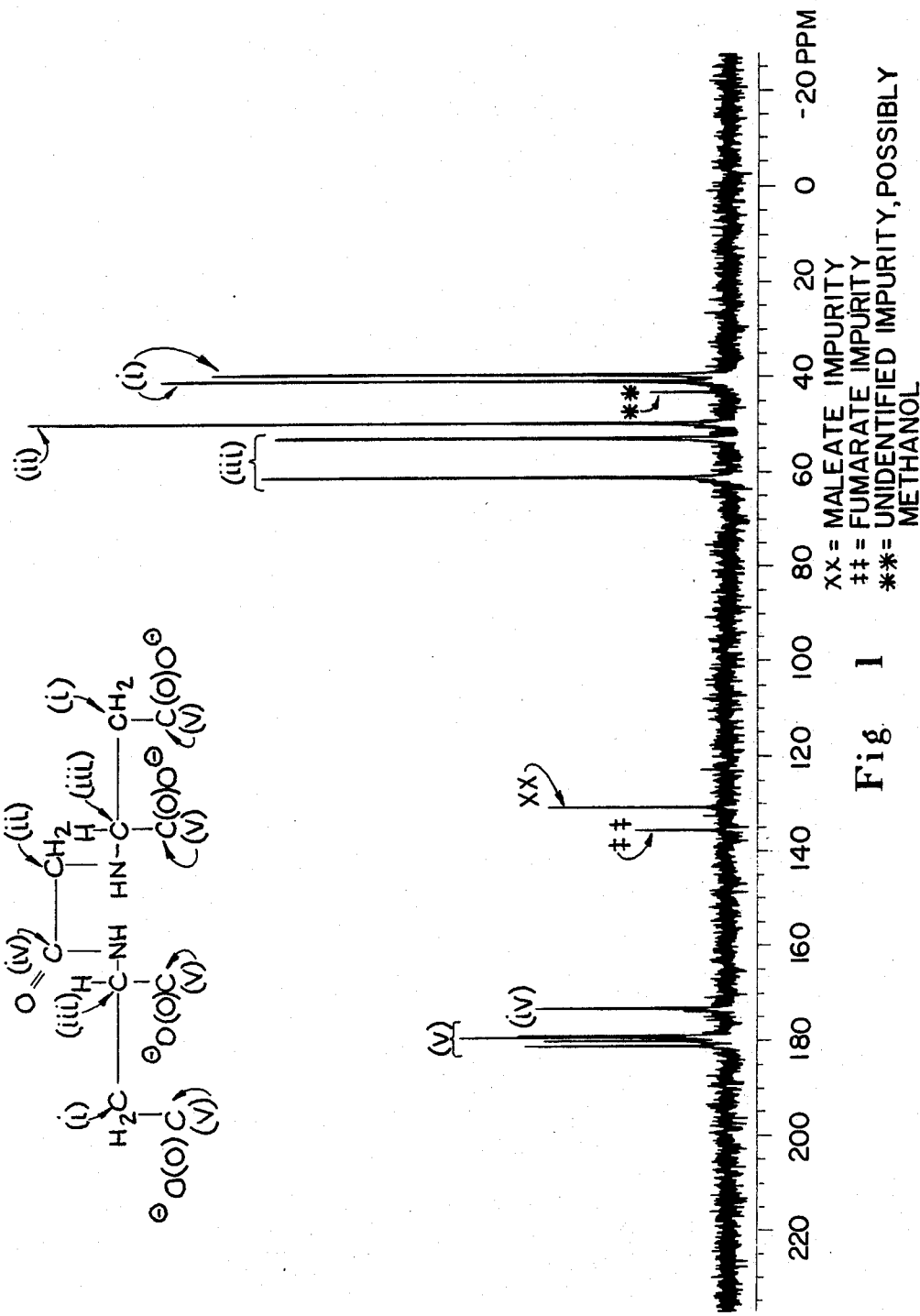
FIG. 1 is a $^{13}C$ Nuclear Magnetic Resonance (NMR) spectrum, in water/ deuterium oxide at pH 9, of a chelating agent composition containing high levels of OEDBA and small amounts of organic impurity (primarily maleate and fumarate) the composition is made according to the general Method 2 and specific illustration thereof (Example V) described hereinafter.

The present invention encompasses the tetraprotic acid $H_4$(OEDBA), i.e., N,N'-(1-oxo-1,2-ethanediyl)-bis-(aspartic acid), and the partial-salts and salts of OEDBA, especially those monobasic, dibasic, tribasic or tetrabasic salts wherein all cations are water-dissociable monovalent cations. Such cations can be organic or inorganic. An alternative name for the tetraanion OEDBA is "glycinamide - N,N'- di(succinate)", giving the (perhaps more felicitous) acronym "GADS". The preferred OEDBA salts are illustrated by the tetrasodium, tetralithium, tetrapotassium, ammonium, tetra(tetramethylammonium), tetra(tetraethylammonium), tetra(tetrapropylammonium), tetra(tetrabutylammonium), and tetra(trimethylammonium) salts, the tetrasodium salt being most highly preferred, inter alia, on grounds of economy. Other highly preferred salts (more exactly, partial salts) are the trisodium salt, the disodium salt and the monosodium salt. It is also in accordance with the invention to have a salt of OEDBA wherein the cations are a mixture of the above-recited cations. These illustrations of particular salt forms of OEDBA should not be considered limiting: other salts, such as OEDBA salts with alkanolamines, the monoethanolammonium OEDBA salts included, are also useful, especially in liquid detergent applications.

OEDBA has more than one stereoisomeric form. The stereoisomerism will more readily be appreciated by reference to the simpler compound, aspartic acid. The latter occurs as two stereoisomers: a naturally occurring L- stereoisomer and a D-stereoisomer. In structural terms, OEDBA can be viewed as the product of attaching two aspartic acid moieties to a 1-oxo-1,2-ethane moiety; or, equally well, as the product of N,N'-substituting glycinamide with two succinic acid moieties. Using the former, aspartic acid-based view of the OEDBA structure, it can be seen that four stereoisomers exist, namely an S,S'-isomer, an R,R'-isomer, an R,S'-isomer and an S,R'-isomer. Each of these OEDBA stereoisomers is encompassed by the invention.

Independently from stereochemical considerations, OEDBA compounds, which are not symmetrical and contain one amino-nitrogen atom and one amido-nitrogen atom (as distinct from the two amino-nitrogen atoms in well-known chelating agents such as EDTA) contain an OEDBA moiety having the following formula:

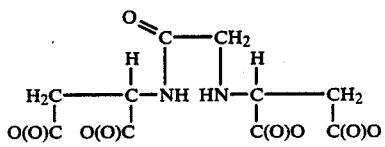

There exists more than one possible method for unambiguously naming OEDBA compounds. As illustrated by compounds X$_4$(OEDBA) wherein X is H or Na, they can be considered as disuccinates since they contain two succinic acid or succinate salt moieties having the formula:

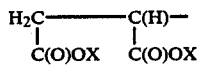

Such OEDBA compounds can equally be termed bis(aspartate) derivatives, since they contain two aspartate moieties having the formula:

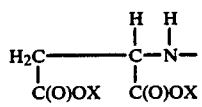

In the latter instance, what remains has the formula:

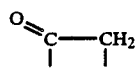

As embodied in OEDBA, this can properly be named a 1-oxo-1,2-ethanediyl moiety, since it is a 1-oxo-1,2-ethane moiety found covalently bonded to each of two nitrogen atoms (hence "diyl").

Each cation X in acid or salt forms of the above-identified OEDBA structure can, in the simplest embodiment, be dissociated in water, so that OEDBA is in the tetra-anion form. Alternatively, each X can be H: then OEDBA is in the tetraprotic acid form. The OEDBA structure as depicted supra will not be considered limiting with respect to the formation, via chemical equilibria, of various charged or neutral forms inherently proper to OEDBA, such as zwitterions or protonated amine forms, across the pH spectrum in aqueous solution. For example, the parent aspartic acid is well known to form zwitterions at acid pH.

In the preferred embodiments of X$_4$(OEDBA), each X is a water-dissociable cation selected from the group consisting of H$^+$, Na$^+$, K$^+$, Li$^+$ and R$_i$N(H)$_{4-i}{}^+$ and mixtures thereof. The integer i can be 0, in which instance R$_i$N(H)$_{4-i}{}^+$ corresponds with the ammonium cation; more preferably, i is any of 1, 2, 3 and 4. When one or more groups R is/are present, i.e., when i is non-zero, R is preferably a compatible hydrocarbyl residue such that the cation R$_i$N(H)$_{4-i}{}^+$ is water-dissociable. When the OEDBA salt is to be used as a bleach-stabilizer, the preferred cation is inorganic, e.g., sodium. Preferred organic cations R$_i$N(H)$_{4-i}{}^+$ include those having i=4; all groups R are saturated, e.g., methyl, ethyl, propyl or butyl. In the most highly preferred forms of OEDBA, each cation X is selected from H$^+$ and Na$^+$.

DETAILED DESCRIPTION OF THE FIGURES

Unless otherwise specifically noted, the positions, i.e., chemical shifts, of all resonances in the Nuclear Magnetic Resonance (NMR) spectra are quoted relative to tetramethylsilane, external standard=0 parts per million (ppm). Downfield shifts are positive.

Figure 2:
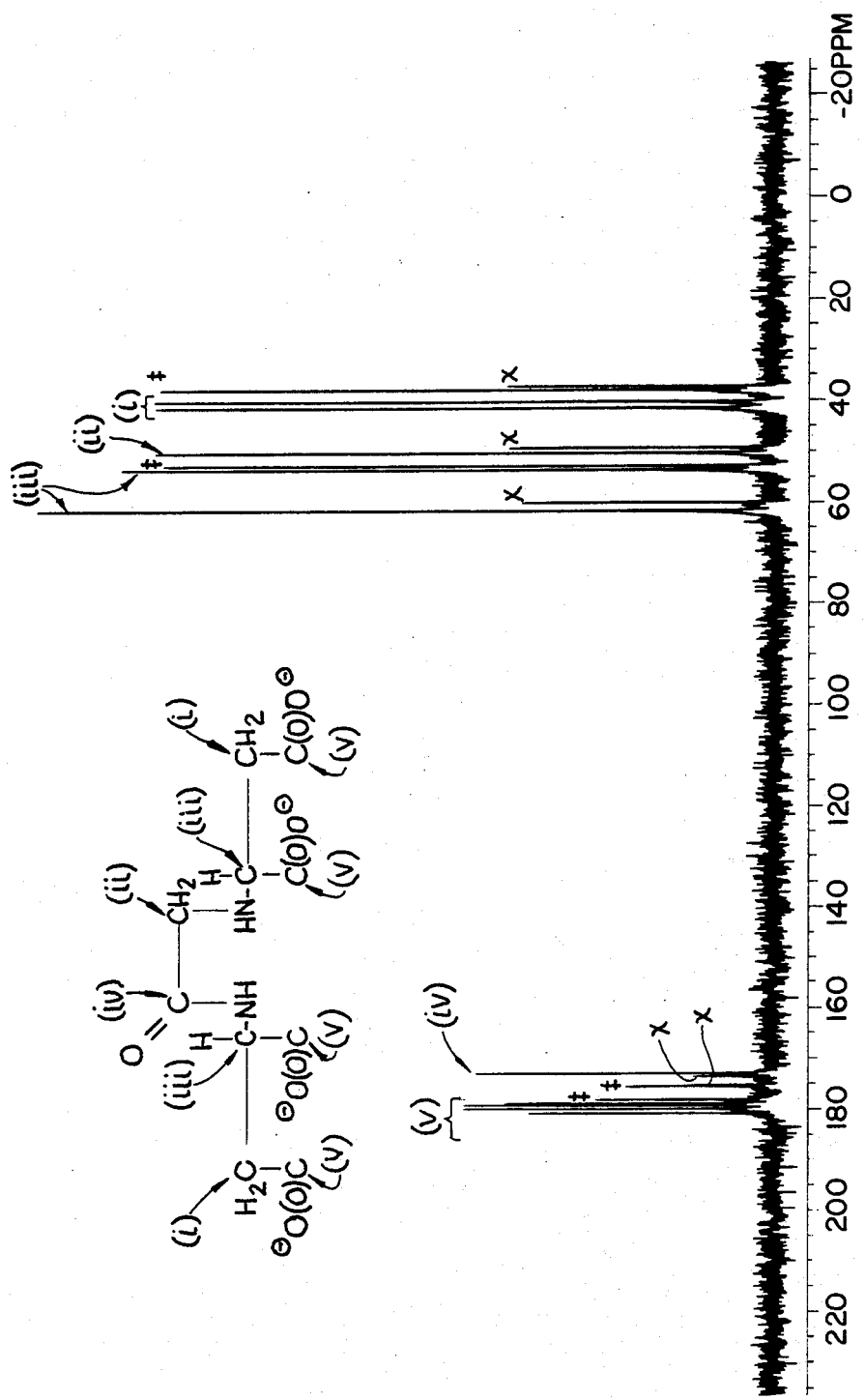
FIG. 2 is a $^{13}C$ Nuclear Magnetic Resonance (NMR) spectrum, in water/deuterium oxide at pH 9, of a composition containing high levels of OEDBA and, as compared with FIG. 1, a different, higher-level impurity, namely the known compound carboxymethylaspartate: the OEDBA composition is made according to the general Method 1 and specific illustration thereof (Example I) described hereinafter. Each of the Figures is produced using a General Electric QE-300 NMR Spectrometer operating at 75.480824 MHz. The probe temperature is ambient, the pulse width is 5.67 microsecond (30 degrees). The acquisition time is 0.819 seconds and the recycle time is 1 second. In each Figure, OEDBA presents ten distinct $^{13}C$ NMR resonances, which are labelled (i)-(v) according to chemical type. The number and the position (chemical shift) of the resonances is consistent with the unique structure of OEDBA, which has low molecular symmetry The spectra are reproducible, however the practitioner should note there is some pH dependence of chemical shift: unless otherwise indicated, spectra should be obtained at pH 9.0 to reproduce the positions of the resonances shown in the Figures and referred to hereinafter in the specification.

The ten OEDBA resonances in each of FIG. 1 and FIG. 2 occur at the following positions:

| Type  | FIG. 1 (ppm) | FIG. 2 (ppm) |
|-------|--------------|--------------|
| (i)   | 39.7         | 39.7         |
| (i)   | 41.0         | 41.1         |
| (ii)  | 49.8         | 49.9         |
| (iii) | 53.1         | 53.1         |
| (iii) | 61.2         | 61.3         |
| (iv)  | 172.8        | 172.9        |
| (v)   | 178.7        | 178.7        |
| (v)   | 179.1        | 179.1        |
| (v)   | 179.8        | 179.8        |
| (v)   | 180.7        | 180.9        |

FIG. 1 is a $^{13}$C NMR spectrum, in water/deuterium oxide at pH 9, of a chelating agent composition containing high levels of OEDBA. the composition is made according to the general Method 2 and specific illustration thereof (Example V) described hereinafter. As noted, FIG. 1 contains ten resonances attributed to OEDBA. FIG. 1 also shows three low-level impurity resonances. Two of these are identified as the well-known materials maleate and fumarate. This can be confirmed by adding authentic samples of maleate or fumarate: no new resonances are observed and the intensity of the resonances identified as maleate and fumarate in FIG. 1 increase. Such confirmation of the identity of impurities by adding known materials is referred to hereinafter as "spiking". In FIG. 1, there is one unidentified impurity resonance: this resonance is believed to be due to methanol, consistent with the hydrolysis step in the synthesis (see the Experimental hereinafter). The assignment of the ten OEDBA resonances is made as follows: The four resonances labelled (v) in FIG. 1 occur at 180.9, 179.8, 179.1, and 178.7 ppm (parts per million relative to tetramethylsilane external standard). Based on chemical shift, these resonances are assigned to the four carboxylate-type carbon atoms in the OEDBA molecule. The unique carbonyl resonance at 172.9 ppm, labelled (iv) in the Figure, is assigned to the amide carbonyl atom of OEDBA on the basis of comparison to the chemical shift of carbon atoms having a similar chemical environment in simple peptides. There remain five resonances in the general region 30 ppm to 65 ppm. Using the APT (Attached Proton Test) technique described by Patt and Shoolery, J. Magn. Reson., Vol. 46, pages 535–539, 1982, it is determined that only the resonances at 53.1 and 61.3 parts per million (ppm), labelled (iii) in FIG. 1, are CH resonances. These two resonances are assigned to the two carbon atoms directly bonded to nitrogen in the OEDBA molecule.

The resonance at 49.9 ppm, labelled (ii) in FIG. 1, is assigned to the unique methylene carbon atom situated adjacent to the amide carbonyl and to the amino nitrogen in OEDBA. The resonances at 39.7 ppm and 41.1 ppm, labelled (i) in FIG. 1, are assigned to the remaining two methylene carbon atoms. The fact that ten distinct resonances are observed and the positions of these resonances are fully consistent with the unusual low-symmetry chemical structure of OEDBA.

FIG. 2 is a $^{13}$C Nuclear Magnetic Resonance (NMR) spectrum, in water/deuterium oxide at pH 9, of a composition containing high levels of OEDBA and, as compared with FIG. 1, a different, higher-level impurity, namely the known compound carboxymethylaspartate: the OEDBA composition is made according to the general Method 1 and specific illustration thereof (Example I) described hereinafter. The positions of the ten resonances due to OEDBA in FIG. 2 are, within the limit of experimental error, fully consistent with those observed in FIG. 1. See the numeric comparison of the OEDBA resonances from the two Figures. The identity of the carboxymethylaspartate impurity resonances in FIG. 2 can be confirmed by "spiking" with carboxymethylaspartate. FIG. 2 also contains resonances assigned to an unreacted starting-material, L-aspartate: the identity of the L-aspartate resonances can also be determined by spiking. The ten consistent OEDBA resonances in each of FIGS. 1 and 2 confirm that identical OEDBA is made by two independent synthetic routes, namely Method 1 and Method 2.

Synthesis of OEDBA: Discovery of OEDBA, including the acid and tetrasodium N,N'-(1-oxo-1,2-ethanediyl)-bis-(aspartate), results from a detailed investigation of the products from reacting aspartic acid with glyoxal bisulfite, a commercially available, relatively inexpensive reactant, under a variety of conditions. It was thought likely that sulfonate-containing products, such as N,N'-(1,2-disulfono-1,2-ethanediyl)bis-(aspartic acid):

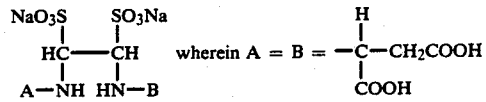

could be made by such reactions. The tetra-carboxylate form of this product can be named ethylenediamine disulfonate disuccinate (EDDS.DS).

However, there are other likely structures for a product of reacting glyoxal bisulfite and aspartic acid. These alternative structures include a mono- or di-imine (Schiff base), as illustrated by the following structures, respectively:

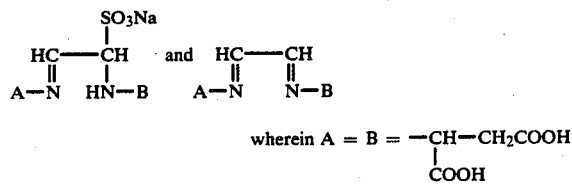

Such Schiff base condensation products would be consistent with a reaction of the amino function of aspartic acid with glyoxal-derived aldehyde moieties Such aldehyde (i.e., CHO) moieties are among the equilibrium species in glyoxal bisulfite-aspartic acid reaction mixtures, in consequence of the following equilibria between glyoxal-sodium bisulfite addition compound (i.e., glyoxal bisulfite) and glyoxal - sodium bisulfite mixtures:

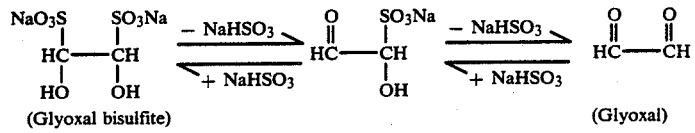

(Glyoxal bisulfite) (Glyoxal)

Instead of the expected products, it transpires that the reaction of aspartic acid with glyoxal bisulfite produces OEDBA as the major product, even then only under carefully controlled conditions. The OEDBA structure is verified by analyzing and comparing HPLC chromatograms, $^{13}$C NMR spectra, and mass spectral data for OEDBA derivatives produced independently by this and another method herein elaborated. The two methods are outlined below:

Method 1

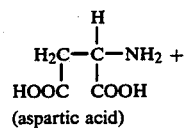
(aspartic acid)

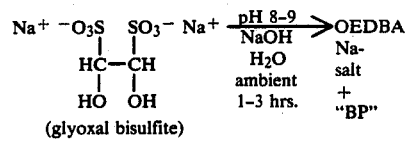

(where "BP" represents unreacted aspartate plus carboxymethyl-aspartate byproduct).

Method 2

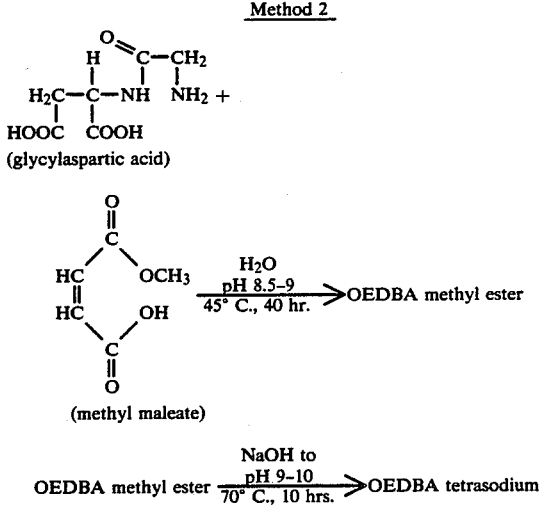

(glycylaspartic acid)

(methyl maleate)

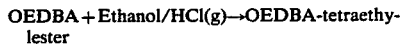

As is shown in the Method 1 synthesis outline, the preferred stoichiometry is 2 moles aspartate per mole of glyoxal reactant. The major byproduct in the Method 1 synthesis is carboxymethylaspartate, a compound which is known and has been used as a builder in detergent compositions, but is a poor chelating agent or sequestrant. For comparison, in the method 2 synthesis, although some maleate and fumarate impurity is commonly identified, the yields are very high (90% or better).

In the above, OEDBA methyl ester is isolable as a stable intermediate; the ester and its simple di-, tri- and tetra-methyl homologs are encompassed by the instant invention. Other simple esters can readily be made, such as by the following reaction:

OEDBA+Ethanol/HCl(g)→OEDBA-tetraethylester

Returning in more detail to the Method 1 OEDBA synthesis, OEDBA in the crude, sodium salt form can be prepared by reacting aspartic acid (the natural or synthetic L-stereoisomer is preferred on grounds of economy) with glyoxal bisulfite in a basic, aqueous reaction medium. The glyoxal bisulfite can equally well be provided "in situ", as the product of reacting glyoxal with a sulfating agent, such as sodium bisulfite or $SO_2$.

The OEDBA synthesis is pH sensitive for which reason the two acidic reactants (aspartic acid and glyoxal bisulfite) should not simply be lumped together in the absence of base: the resulting low pH favors the production of carboxymethylaspartate byproduct. It is equally undesirable to use other methods of starting or maintaining the reaction at a pH less than 7. It is also undesirable to start or maintain the reaction at a pH greater than 10 since such high pH appears to suppress the production of OEDBA and aspartic acid is left unreacted. Very preferably, the reaction pH is maintained between 8 and 9.

Temperature is not particularly critical in the Method 1 synthesis, though naturally, the practitioner will avoid boiling for extended periods, etc., since the desired product contains an amide which may be destroyed. In any event, excellent results can typically be obtained by conducting the Method 1 synthesis at or about ambient temperature.

In the Method 1 synthesis, concentrations of the reactants can vary. It is preferred to have a concentration of the sum of the reactants in the range about 35%–40%.

Most preferably, the aspartic acid is dissolved in water in the presence of enough sodium hydroxide to have an initial pH in the range from 8.5 to about 9. Within this pH range, OEDBA production is faster at the high end (i.e., towards pH 9); reaction times of from about 1 to about 3 hours are typical. Glyoxal bisulfite should be added (preferably portionwise and slowly) to the aspartic acid-sodium hydroxide solution while the pH is monitored and maintained within the specified range by adding compensating amounts of sodium hydroxide.

More sophisticated "pH-statting" methods can be used to keep the pH constant. For example, electronic or electrochemical pH controlling means may be relied on, as illustrated by a commercially available titrator or controller such as a Mettler DL25 Autotitrator or a Fisher Model 450 Titration Controller.

Typically, after carrying out the OEDBA synthesis, the solution containing the crude OEDBA is subjected to evaporation (suitable means are illustrated by a rotary evaporator) to yield a light yellow, OEDBA-containing powder. The color is believed to be due to trace impurities. Yield of OEDBA based on aspartate, i.e., % conversion of aspartate to OEDBA, is typically about 50% (HPLC). Analysis shows that the powder has an OEDBA activity, i.e., content by weight, which is typically about 35%. The crude product composition from the Method 1 synthesis also typically contains about 5% unreacted aspartate and about 10% byproduct carboxymethylaspartate. The balance of the powder is inorganic, and is comprised of (1) inorganic cations (in an amount which charge-balances the OEDBA, aspartate and carboxymethylaspartate) and (2) inorganic salts.

For comparison with the above-outlined procedure, the reverse addition, i.e., adding a solution of aspartic acid at pH 9 to a solution of glyoxal bisulfite, generally seems to produce more of the unwanted carboxymethylaspartate byproduct, and proportionately less of the desired OEDBA product.

In view of the relatively lower cost of the starting-materials, the Method 1 process for preparing OEDBA may have considerable economic advantages over the second preparative method, which involves reacting glycylaspartic acid and methyl maleate. However, without further refinement of the Method 1 process, Method 2 is currently superior in terms of outright yield of OEDBA and lower content of unreacted organic starting-materials and organic byproducts. The inorganic components, such as metal cations, are typically inert, and can generally be left in the product without ill-effect, except that excess bisulfite, if present, is most preferably converted to inert sulfate or bisulfate, or is physically removed. The OEDBA compositions obtained by this second method typically have a 90% yield of OEDBA. There is usually a little maleate and fumarate impurity, but importantly, no carboxymethylaspartate is detectable.

In more detail, the preferred embodiment of the Method 2 synthesis, as can be seen from the outline, entails treating glycylaspartate with methyl maleate in aqueous alkaline solution, the pH preferably being in the range 8.5–9. Reaction temperatures may vary: high temperatures (e.g., 100° C.) are preferably avoided. At relatively low temperatures, e.g., 20° C., reaction times tend to increase. Excellent results are secured in the temperature range about 40° C. to about 50° C.; typical reaction times are about 25 hours to about 50 hours. Preferably, the Method 2 synthesis is carried out at relatively high concentrations, e.g., the sum of reactants produces an aqueous concentration of 20%, or higher, always provided that concentrations are not such as to occasion precipitation of the reactants. Levels of maleate and/or fumarate tend to be lowest in the unpurified product OEDBA of Method 2 when the synthesis is carried out at the above-illustrated temperatures, within the above-identified preferred pH range. As in Method 1, pH-"statting" can be used to advantage.

In terms of order of addition or combination of the reactants in the Method 2 synthesis, it is preferable to add the methyl maleate to an aqueous alkaline glycylaspartate solution.

It is anticipated that the Method 2 synthesis can equally well be carried out using ethyl maleate, propyl maleate, or butyl maleate as a replacement for methyl maleate. Likewise, it is possible to substitute for glycylaspartate a lower alkyl ester of glycylaspartate. Whatever substitution of reactants is carried out, it is important to keep them water-soluble. For example, use of a hexadecyl maleate ester instead of methyl maleate is not contemplated, because it is well known that long-chain alkyl esters have limited water-solubility.

However prepared, it is possible to further purify the OEDBA by re-esterifying with ethanol and conventionally chromatographing to secure the substantially pure tetraethyl ester. This can be rehydrolyzed with a variety of bases, e.g., NaOH or KOH, to make the corresponding OEDBA salts. However, such purification is not generally essential (there may be exceptions such as in pharmaceutical applications), and the unpurified OEDBA can normally be used directly in a variety of circumstances where a chelating agent is needed, especially in detergent compositions, as will shortly be illustrated.

The identity of OEDBA is further confirmed by Fast Atom Bombardment Mass Spectroscopy (FAB) of OEDBA (tetraethyl ester) and of OEDBA (permethylated). OEDBA can readily be permethylated using the known reagent system of methanol/diazomethane in ether. FAB spectra can be obtained using a VG ZAB-2F mass spectrometer operating in FAB mode. The following data are obtained:

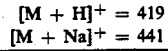

OEDBA (tetraethylester) Mass Spectral Data Prepared as in Example VI:

$[M + H]^+ = 419$
$[M + Na]^+ = 441$ wherein M represents the parent ion, tetraethyl-OEDBA OEDBA (permethylated) Mass Spectral Data (permethylated with 50:50 wt:wt methanol/diazomethane in ether):

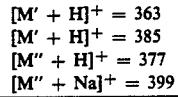

$[M' + H]^+ = 363$
$[M' + H]^+ = 385$
$[M'' + H]^+ = 377$
$[M'' + Na]^+ = 399$

Detergent Compositions, Bleach Compositions, Chelating Agent Compositions and Other Cleaning Compositions - General Considerations Detergent compositions, bleach compositions and other cleaning or sequestrant compositions according to the present invention all generally comprise 0.05% to about 99% by weight of OEDBA. In specifying this range of percentages by weight, and other percentages by weight of OEDBA in detergent compositions, bleach compositions, cleaning compositions and sequestrant (chelating agent) compositions illustrated hereinafter, there is no carboxymethylaspartate, aspartate, maleate, fumarate, inert salt or other material included in the percentages given, only OEDBA and a charge-balancing amount of hydrogen, sodium or potassium. Unless otherwise specifically noted, the OEDBA content of all these various compositions is unambiguously specified by convention on a 100% OEDBA (acid) basis. When the formulator wishes to use relatively inexpensive forms of OEDBA such as unpurified OEDBA resulting directly from the Method 1 synthesis, or OEDBA containing other cations, salts or impurities, the salt content and/or less than 100% purity will be taken into account and compensated for by using a commensurately greater weight of the particular form of OEDBA chosen. Clearly, though the method is more expensive, in view of the higher yield and purity of OEDBA secured by the Method 2 synthesis, best performance per unit weight is obtained when the Method 2-synthesized OEDBA is formulated in detergent, bleach stabilizer or chelating agent compositions, usually as the acid or sodium salt.

Detergent compositions in accordance with the invention generally comprise from about 1% to about 99.98% (typically 5% to 30%) of a conventional detersive surfactant, and from 0.05% to 99% by weight of OEDBA.

When the detergent composition further comprises a conventional builder, as further illustrated hereinafter, the OEDBA is typically present in the detergent compositions at a relatively low level (0.05% to 5%; preferably 0.1% to 0.8%) for its ability to sequester or otherwise control transition metal solutes, suspensions or precipitates, especially those of iron, copper and manganese. However, OEDBA may be relied on as the primary builder or cobuilder, in which case the OEDBA content of the detergent composition can vary widely, such as from about 1% to about 50%.

Bleach compositions of the present invention will generally comprise from about 1% to about 99.95%, preferably about 3% to 99.2%, of a conventional bleaching agent, and about 0.05%, more typically 0.1% to 0.8%, of OEDBA. Suitable bleaches may be activated or non-activated. Non-activated bleaches are further illustrated by percarbonate (including, but not limited to, sodium percarbonate), perborate (including, but not limited to, sodium perborate mono- and tetrahydrates), peroxides (including, but not limited to, sodium peroxide, hydrogen peroxide, urea peroxide, and the like), persulfates (including, but not limited to, potassium persulfate) and perphthalates (including, but not limited to magnesium monoperphthalic acid, known in commerce as INTEROX H-48). Activated bleaches, i.e., bleach materials containing various bleach "activators", include any of the above-illustrated bleaches in combination with a bleach activator. Suitable bleach activators are illustrated by the well-known tetraacetylethylenediamine, by nonanoyloxybenzenesulfonate and by isononanoyloxybenzenesulfonate, as disclosed in European patent application EP Ser. No. 195663 A2, published Sept. 24, 1986, incorporated herein by reference.

Surfactant-free cleaning compositions according to the invention include built cleaning compositions suitable for hard-surface cleaning, such as certain automatic dishwashing agents and kitchen or bathroom cleaners. Such cleaning compositions generally comprise from about 1% to about 99.95%, preferably about 90% to about 99%, of a conventional builder and at least about 0.0.5%, typically 0.1% to 5% OEDBA.

Typically, fully-formulated detergent compositions herein will comprise from about 5% to about 30% by weight of a detersive surfactant, especially mixtures of nonionic and anionic, and optional cationic surfactants; from about 5% to about 40% by weight of one or more conventional builders, especially nonphosphorus builders; optionally, 3% to 30% by weight of a bleach, especially a perborate (or perborate plus activator) bleach; and typically, from 0.1% to 0.8% by weight of OEDBA, preferably as the tetrasodium or other water-dissociable salt.

As noted, the OEDBA can be used as the major builder in detergents, especially liquid detergents. When used as such, OEDBA will preferably comprise 5% to 35% of such compositions.

The following exemplifies typical materials for use in fully-formulated detergent compositions, but is not intended to be limiting thereof.

Detersive Surfactants: The detergent compositions of this invention contain organic surface-active agents which have a soil-cleaning effect. Such materials are termed "detersive surfactants", the adjective "detersive" serving to distinguish them from those surface-active materials, including several common soil release agents and fabric softeners, which are well-known to be primarily useful not as cleaning agents but for more specialized purposes. This is not to say that softeners such as ditallowdimethylammonium chloride and soil release agents such as oligomeric polyesters cannot be used herein as adjuncts for their usual useful purposes: see the Examples hereinafter.

Detersive surfactants useful herein include well-known synthetic anionic, nonionic, amphoteric and zwitterionic surfactants. Typical of these are the alkylbenzenesulfonates, alkyl- and alkylether sulfates, paraffin sulfonates, olefin sulfonates, amine oxides, alpha-sulfonates of fatty acids and of fatty acid esters, alkyl glycosides, ethoxylated alcohols and ethoxylated alkyl phenols, and the like, which are well-known from the detergency art. In general, such detersive surfactants contain an alkyl group in the $C_9$–$C_{18}$ range; the anionic detersive surfactants can be used in the form of their sodium, potassium or triethanolammonium salts. Standard texts such as the McCutcheon's Index contain detailed listings of such typical detersive surfactants. $C_{11}$–$C_{14}$ alkylbenzene sulfonates, $C_{12}$–$C_{18}$ paraffin-sulfonates, and $C_{11}$–$C_{18}$ alkyl sulfates, alpha-sulfonated fatty acid methyl esters and alkyl ether sulfates are especially preferred in the detergent compositions of the present type.

Also useful herein are the water-dissociable soaps, e.g., the common sodium and potassium coconut or tallow soaps well-known in the art. Unsaturated soaps such as alkyl soaps may be used, especially in liquid formulations. Saturated or unsaturated $C_9$–$C_{16}$ hydrocarbyl succinates are also effective.

Mixtures of the anionics, such as the alkylbenzene sulfonates, alkyl sulfates and paraffin sulfonates, with $C_9$–$C_{16}$ ethoxylated alcohol surfactants are preferred for through-the-wash cleansing of a broad spectrum of soils and stains from fabric.

Combinations of anionic, cationic and nonionic surfactants can generally be used. Such combinations, or combinations only of anionic and nonionic surfactants, are preferred for liquid detergent compositions. Such surfactants are often used in acid form and neutralized during preparation of the liquid detergent composition. Preferred anionic surfactants for liquid detergent compositions include linear alkylbenzene sulfonates, alkyl sulfates, and alkyl ethoxylated sulfates. Preferred nonionic surfactants include alkyl polyethoxylated alcohols.

Anionic surfactants are preferred for use as detergent surfactants in granular detergent compositions. Preferred anionic surfactants include linear alkylbenzene sulfonates and alkyl sulfates. Combinations of anionic and nonionic detersive surfactants are especially useful for granular detergent applications.

Conventional Builders: The preferred builders used in the practice of this invention include known materials which bind calcium and/or magnesium effectively. Familiar transition-metal ion sequestering agents, e.g., the amine chelants, as illustrated by ethylenediaminetetraacetate (EDTA) or diethylenetriamine pentaacetate (DETPA), or phosphonate chelants as illustrated by ethylenediamine tetraphosphonate, can be coformulated with the builder, at their customary levels, although OEDBA makes their use unnecessary. Tripolyphosphate or pyrophosphate builders serve as excellent illustrations of builders which bind calcium and magnesium very effectively. Importantly, various nonphosphorus builders are useful herein. Included among these by way of exemplification, but not limitation, are 1–10 micron Zeolite A, which is especially effective for calcium-binding, and sodium carbonate and sodium silicate. The latter binds magnesium and is also effective as a washing machine anti-corrosion agent and detergent granule crispener. Water-soluble nonphosphorus builders useful herein include a highly preferred ether-carboxylate, 2,2'-oxodisuccinate, which is disclosed in U.S. Pat. No. 3,128,287, Berg, issued Apr. 7, 1964; U.S. Pat. No. 3,635,830, Lamberti et al, issued Jan. 18, 1972, and U.S. Pat. No. 4,798,907, MacBrair, Jr. et al, issued Jan. 17, 1989, all incorporated herein by reference. Other useful water-dissociable nonphosphorus builders include the tartrate mono- and di-succinates of U.S. Pat. No. 4,663,071, Bush et al, issued May 5, 1987 incorporated by reference; citrates; $C_8$–$C_{14}$ hydrocarbyl succinates; and mixtures thereof. Inorganic nonbuilder salts, such as sodium sulfate, can also be present. Lists of builders useful herein can be had by reference to U.S. Pat. No. 4,704,233.

Bleaches: As noted, various well-known oxygen bleaching agents (especially fiber and fabric bleaches) are well-known and can be used herein. For laundry detergents, the sodium perborate mono- and tetra-hydrates are preferred, although the percarbonates and persulfates are also useful, particularly when OEDBA helps remove iron from the system. Peroxide bleaches, such as hydrogen peroxide, may also be used in conjunction with OEDBA.

Detersive Adjuncts: Detergent compositions herein can contain various ingredients which aid in their cleaning performance. For example, it is highly preferred that the laundry compositions herein also contain enzymes to enhance their through-the-wash cleaning performance on a variety of soils and stains. Amylase and protease enzymes suitable for use in detergents are well-known in the art and in commercially available liquid and granular detergents. Commercial detersive enzymes (preferably a mixture of amylase and protease) are typically used at levels of 0.001 % to 2%, and higher, in the present cleaning compositions. Detersive adjuncts especially useful in the practice of the invention are further illustrated in, but not limited by, the Examples hereinafter.

Moreover, the cleaning compositions herein can contain, in addition to ingredients already mentioned, various other optional ingredients typically used in commercial products to provide aesthetic or additional product performance benefits. Typical ingredients include pH regulants, perfumes, dyes, bleaches, optical brighteners, polyester soil release agents, hydrotropes and gel-control agents, freeze-thaw stabilizers, bactericides, preservatives, suds control agents, bleach activators and the like. Fabric softeners, especially clays and mixtures of clays with various amines and quaternary ammonium compounds, can all be used. Such matters are well-known from the patent literature and in commercial practice.

The various OEDBA-containing bleach compositions, detergent compositions, chelating agent compositions and other cleaning compositions herein are all prepared using conventional techniques, well-known to the formulator of commercial detergent and bleach products.

In a through-the-wash fabric cleansing mode, the detergent compositions, builder compositions or chelating agent compositions herein are typically used at a concentration of about 0.10% to about 2.5%, in an aqueous laundry bath, typically at pH 7-11, to cleanse fabrics. The laundering can be carried out by agitating fabrics with the present compositions over the range from 5° C. to the boil with excellent results, especially at temperatures in the range from about 35° C. to about 80° C.

The following Examples illustrate the practice of this invention, but are not intended to be limiting thereof. Unless otherwise indicated, pH is measured using a combination pH electrode, Fisher Scientific, Model 13-620-290, for small samples including NMR samples; and using a combination pH electrode, Fisher Scientific, Model 13-620-108, in any other circumstance. The electrodes are calibrated using standard buffer solutions, pH 10, 7 and 4. When not in use, the electrodes are stored in pH 7 buffer. Unless otherwise indicated, pH measurements are at ambient, ca. 27° C.

EXAMPLE I

Preparation of OEDBA, Method 1: L-aspartic acid (66.58g, 0.500 moles, Aldrich) is stirred in 250 ml. water and sodium hydroxide (50 wt % in water, 48.2g, 0.603 moles, J. T. Baker) is added to bring the solution to pH 9.0. Glyoxal bisulfite (71.07 g, 0.250 moles, Aldrich) is added in small portions over one hour. During this addition, more sodium hydroxide (50 wt % in water, 47.5 g, 0.59 moles, J. T. Baker) is progressively co-added so as to keep the pH as closely constant (9.0) as possible. Throughout the addition, the temperature is in the range from 20° C. to 40° C. The reaction is essentially complete within about 3 hours. The resulting solution is translucent and golden-yellow in color.

A $^{13}C$ NMR spectrum of this solution, such as that depicted in FIG. 2, may be obtained as follows: evaporate a small aliquot. Weigh out about 0.8 grams. Dissolve in about 4 ml. deuterium oxide ($D_2O$); adjust the pH with sodium hydroxide (typically 0.34 ml., 1 Normal, aqueous) to pH 9.0. FIG. 2 shows ten resonances due to OEDBA, and resonances due to unreacted L-aspartate and a byproduct impurity, carboxymethylaspartate (CMA). The OEDBA yield is roughly estimated as about 35%, based on $^{13}C$ and HPLC analysis.

EXAMPLE II

Enrichment of the OEDBA content of the product of Example I: The solution of Example I is treated with aqueous HCl or $H_2SO_4$, in an amount sufficient to lower the pH to about 3. The solution is refrigerated for 1-2 days. L-aspartic acid crystallizes and is removed by filtration. A $^{13}C$ NMR spectrum of the resulting solution confirms that the relative proportion of OEDBA to L-aspartic acid is significantly increased. Byproduct CMA is still present. The solution is evaporated under reduced pressure using a rotary evaporator at a temperature not more than about 60° C. Upon concentration, solid sodium chloride, resulting from the acid neutralization of the reaction mixture, precipitates and is removed by filtration. Additional aqueous HCl is now added to adjust the pH to 3, and L-aspartic acid crystallizes. The mixture is again filtered, the L-aspartic acid is discarded, and the filtrate is taken to dryness using a rotary evaporator to yield 61.8 g yellow solids. HPLC analysis shows this material to be about 50% OEDBA.

EXAMPLE III

Preparation of OEDBA from D-aspartic acid D-aspartic acid is substituted for L-aspartic acid in Example I. The procedure is otherwise identical to that of Example I. Whereas the product OEDBA of Example I is the S,S'- stereoisomer, the product OEDBA in the instant Example is the R,R'- stereoisomer.

EXAMPLE IV

Preparation of OEDBA from D,L-aspartic acid: An equal weight mixture of D-aspartic acid and L-aspartic acid is substituted for L-aspartic acid in Example I. The procedure is otherwise identical to that of Example I. Whereas the product OEDBA of Example I is the S,S'-stereoisomer, the product OEDBA in the instant Example is a mixture of S,S'-, R,R'-, R,S'- and L- S,R'-stereoisomers.

EXAMPLE V

Preparation of OEDBA, Method 2: (a). Glycylaspartic acid (5.0337 g, 26.47 millimoles, Sigma Chemical) and water (15 ml.) are placed in a flask. The flask is cooled in an ice-bath until the contents are at a temperature of 3° to 5° C. Methyl maleate (3.4545 g, 26.55 millimoles) is added, along with 10 ml. additional water. (The methyl maleate can conveniently be made by conventional reaction of maleic anhydride and methanol.) Sodium hydroxide (50 wt %, J. T. Baker) is added in an amount sufficient to raise the pH to 8.5-9.0. The reaction mixture is allowed to warm to ambient temperature. The pH is now about 8.75. The flask is heated by means of an oil bath at 45° C. for 20 hours. The pH is adjusted to 8.5-9.0 once again, by adding 50% sodium hydroxide, and the reaction is continued at 45° C. for a second period of 20 hrs.

(b). The product of (a), containing crude methyl esters of OEDBA, is hydrolyzed to liberate OEDBA, by adjusting the pH to 9.5–10 and heating at 70° C. for 10 hrs, whereupon $^{13}$C NMR and HPLC analyses of an aliquot demonstrate that OEDBA is present in high yield (90%, or higher). The method for preparing the $^{13}$C NMR sample (pH=9.0, water/D$_2$O) is as reported in Example 1, supra, except that ca. 0.4 grams of the evaporated sample is used, and the pH is 9. FIG. 1 is typical of the $^{13}$C NMR spectrum which is obtained. Detectable impurities are at low levels and are predominantly maleate and fumarate No HPLC or NMR - detectable amount of carboxymethylaspartate (CMA) impurity is present. The OEDBA prepared by this method is conveniently evaporated to dryness under reduced pressure.

EXAMPLE VI

Preparation of the tetraethyl ester of OEDBA: The material of Example I, 34.71 g, and absolute ethanol (500 ml.) are placed in flask submerged in an ice bath. Hydrogen chloride gas is bubbled through the solution for one hour, then the reaction is removed from the ice bath and stirred overnight. The reaction mixture is filtered through a 0.4 micron filter to remove NaCl and the filtrate is concentrated using a rotary evaporator. The resulting oil is dissolved in chloroform and washed with cold Na$_2$CO$_3$ solution and dried with anhydrous Na$_2$SO$_4$ to yield 7.6812 g of a dark but charcoal-decolorizable oil. The tetraethyl ester of OEDBA is characterized by mass spectroscopy (MH+ =419, MNa+ =441).

EXAMPLE VII

Conversion of OEDBA tetraethyl ester to the tetrapotassium salt: The tetraethyl ester of Example VI is hydrolyzed at about 60° C. with aqueous KOH, forming the tetrapotassium salt of OEDBA.

EXAMPLE VIII

Conversion of OEDBA tetraethyl ester to the tetrasodium salt form: The tetraethyl ester of Example VI is decolorized using charcoal and is hydrolyzed at about 60° C. using aqueous NaOH. $^{13}$C NMR spectroscopy of the resulting colorless solution is consistent with free, unesterified tetrasodium OEDBA.

EXAMPLE IX

Preparation of a solid bleach composition containing OEDBA as a bleach performance enhancer: A stable, solid bleach composition embodying OEDBA as bleach performance enhancer is prepared by dry-blending ingredients, as follows.

| Ingredient | Percent (Wt.) |
|---|---|
| OEDBA | 3.0 |
| Sodium Perborate.H$_2$O | 97.0 |

EXAMPLE X

Preparation of a stable liquid bleach composition embodying OEDBA as bleach stabilizer: Such a bleach composition is prepared by dissolving 0.1% (wt.) of OEDBA in 5% aqueous hydrogen peroxide.

EXAMPLE XI

Preparation of a soap composition containing OEDBA which is suitable for use as bars, chips, flakes or granules: Such a soap composition is prepared by plodding 0.56% (wt.) of OEDBA into 99.44% commercial soap (fatty acid salts).

EXAMPLE XII

A detergency builder composition containing OEDBA as chelating agent: Such a detergency builder composition is as follows:

| Ingredient | Percent (Wt.) |
|---|---|
| Zeolite A (1–10 micron) | 96 |
| OEDBA | 4 |

The 96 parts Zeolite A can be substituted by 80 parts Zeolite A and 16 parts anhydrous citric acid, with excellent results.

EXAMPLE XIII

An organic carboxylate builder composition containing OEDBA which is especially compatible with, and useful for coformulation in laundry detergents with, perborate. percarbonate or peracid-activated perborate bleaches: Such an organic builder composition is as follows:

| Ingredient | Percent (Wt.) |
|---|---|
| 2,2'-oxodisuccinate tetrasodium salt (pure) | 90 |
| OEDBA | 10 |

EXAMPLE XIV

An organic carboxylate composition embodying a useful ethercarboxylate builder and OEDBA as sequestrant: Such an organic carboxylate composition is as follows:

| Ingredient | Percent (Wt.) |
|---|---|
| TMS/TDS* | 99 |
| OEDBA | 1 |

*Mixture of tartrate mono- and di-succinate sodium salts prepared according to U.S. Pat. No. 4,663,071.

EXAMPLE XV

A mixed, nonphosphorus builder and sequestrant composition containing OEDBA.. Such a builder and sequestrant composition comprises:

| Ingredient | Percent (Wt.) |
|---|---|
| Zeolite A (1–10 micron) | 70.0 |
| TMS/TDS | 15.0 |
| 2,2'-oxodisuccinate, tetrasodium salt | 14.2 |
| OEDBA | 0.8 |

Fully-formulated detergent compositions containing OEDBA in the manner of this invention are as follows:

EXAMPLE XVI

A liquid detergent composition for household laundry use is as follows:

| Component | Wt. % |
|---|---|
| OEDBA | 0.8 |
| C$_{12.3}$ linear alkylbenzene sulfonic acid (acid form) | 8.3 |
| C$_{14}$–C$_{15}$ alkyl polyethoxylate (2.25) sulfuric acid | 3.3 |
| C$_{12}$–C$_{13}$ alcohol polyethoxylate (6.5) (alcohol and monoethoxylated alcohol stripped) | 5.0 |
| C$_{12}$ alkyltrimethylammonium chloride | 2.3 |
| C$_{12}$–C$_{14}$ saturated fatty acid | 2.9 |
| Citric acid anhydrous | 3.4 |
| Tartrate monosuccinate/disuccinate 85:15 wt:wt, sodium salts, anhydrous | 3.4 |
| Polyester soil release agent: capped (1,2-propylene glycol-co-dimethyl terephthalate) oligomer with av. degree of oligomerization 2.8 based on dimethyl terephthalate; wherein the caps are from CH$_3$(OCH$_2$CH$_2$)$_{30}$OH | 0.8 |
| Protease enzyme (2.0 AU/g activity) | 0.7 |
| Tetraethylenepentamine polyethozylate (15–18) | 1.5 |
| Sodium cumene sulfonate | 2.2 |
| 1,2-propylene glycol | 4.5 |
| Monoethanolamine | 1.0 |
| Ethanol | 1.2 |
| Sodium formate | 0.3 |
| Calcium formate | 0.3 |
| Sodium hydroxide | 2.9 |
| Potassium hydroxide | 1.0 |
| Balance: Distilled water and optionally, perfume, brightener, and colorant: | to 100.00 |

The components are added together with continuous mixing to form the composition. Amounts of sodium and potassium can be varied: the formulation as a whole preferably has a potassium: sodium mole ratio in the range 0.26:1 to 1:1. The pH at 10% concentration is typically 8–8.5. The practitioner may rely on U.S. Pat. No. 4,507,219, Hughes, issued Mar. 26, 1985, incorporated by reference, for detail in connection with the manufacture of liquid detergent formulae into which OEDBA may readily be formulated by mixing, either as an additional ingredient or as a replacement for known chelating agents. Suitable soil release agents are disclosed by Gosselink, U.S. Pat. No. 4,702,857, issued Oct. 27, 1987, incorporated by reference. Anionic soil release agents can be substituted therefor, with excellent results. See U.S. Pat. No. 4,721,580, Gosselink, issued Jan. 26, 1988, incorporated by reference, for examples of anionically capped soil release agents which are suitable. The tetraethylenepentamine polyethoxylate illustrated supra is a clay soil removal agent: see U.S. Pat. No. 4,597,898, VanderMeer, issued July 1, 1986, incorporated herein by reference. For best results, soil release agents are customarily not directly mixed with neat monoethanolamine or other highly acidic or alkaline components. The tartrate monosuccinate/disuccinate builder is disclosed in the hereinabove incorporated U.S. Pat. No. 4,663,071, Bush et al, issued May 5, 1987.

EXAMPLE XVII

A liquid detergent composition for household laundry use is prepared by mixing the following ingredients.

| Component | Wt. % |
|---|---|
| OEDBA | 1.5 |
| C$_{12.3}$ linear alkylbenzene sulfonic acid (acid form) | 9.5 |
| C$_{14}$–C$_{15}$ alkyl polyethoxylate (2.25) sulfuric acid | 3.3 |
| C$_{13}$–C$_{15}$ alcohol polyethoxylate (7) | 11.0 |
| C$_{12}$ alkyltrimethylammonium chloride | 2.3 |
| Dodecenylsuccinic acid | 12.0 |
| Citric acid anhydrous | 0.8 |

| Component | Wt. % |
|---|---|
| Polyester soil release agent: capped (1,2-propylene glycol-co-dimethyl terephthalate) oligomer with av. degree of oligomerization 2.25 based on dimethyl terephthalate) wherein the caps are from CH$_3$(OCH$_2$CH$_2$)$_{18}$OH | 0.6 |
| Protease enzyme (1.5 AU/g activity) | 0.9 |
| Tetraethylenepentamine polyethoxylate (15–18) | 0.3 |
| 1,2-propylene glycol | 1.5 |
| Ethanol | 6.0 |
| Sodium formate | 1.0 |
| Calcium chloride (adjust for 60 ppm in final product) | 0.02 |
| Sodium hydroxide | 3.4 |
| Polydimethylsiloxane (DOW CORNING DB-110A) | 0.003 |
| Opacifier (MORTON WILLIAMS "LYTRON" 621) | 0.22 |
| Balance: Distilled water and perfume, brightener, and colorant as desired: | to 100.0 |

EXAMPLE XVIII

A granular laundry detergent is as follows.

| Ingredient | Percent (wt.) |
|---|---|
| OEDBA | 0.8 |
| C$_{12.3}$ alkyl benzene sulfonate, sodium salt | 10.3 |
| Tallow alcohol sulfate, sodium salt | 10.3 |
| C$_{12-13}$ alcohol (6.5 ethoxylate) | 1.0 |
| Tallow fatty acid | 1.0 |
| Zeolite A (1–10 micron) | 26.0 |
| Protease enzyme (1.5 AU/g) | 0.4 |
| Polyacrylate, sodium salts, av. m.w = 4,500 | 3.1 |
| Sodium silicate, Na$_2$O:SiO$_2$ ratio = 1.6:1, dry basis | 2.2 |
| Sodium carbonate | 15.3 |
| Na$_2$SO$_4$ and minors (color, perfume, brightener) | 20.8 |
| PEG 8000 | 1.0 |
| Sodium perborate.4H$_2$O | 4.0 |
| Water: Balance to: | 100.0 |

EXAMPLE XIX

A phosphated, bleach-and-bleach-activator containing granular laundry detergent relying on OEDBA for enhanced through-wash bleach performance is as follows:

| Ingredient | Percent (wt.) |
|---|---|
| OEDBA | 0.4 |
| C$_{12}$ linear alkyl benzene sulfonate, sodium salt | 9.8 |
| C$_{14}$–C$_{15}$ alcohol sulfate, sodium salt | 4.1 |
| C$_{12-13}$ alcohol (6.5 ethoxylate) | 1.3 |
| Tallow fatty acid | 1.0 |
| Sodium tripolyphosphate | 21.5 |
| Sodium pyrophosphate | 5.2 |
| Protease enzyme (1.5 AU/g) | 0.6 |
| Polyacrylate, sodium salt, av. m.w = 4,500 | 0.65 |
| Sodium silicate, Na$_2$O:SiO$_2$ ratio = 1.6:1, dry basis | 4.2 |
| Sodium carbonate | 22.0 |
| Na$_2$SO$_4$ | 13.2 |
| Brightener, perfume | 0.5 |
| PEG 8000 | 0.4 |
| Sodium perborate monohydrate | 4.0 |
| INOBS* | 5.6 |
| Water: Balance to: | 100.0 |

*Sodium 3,5,5-trimethyl hexanoyl oxybenzene sulfonate, a peracid bleach activator.

EXAMPLE XX

The composition of Example XIX is modified by varying the level of OEDBA over the range from 0.1% to 0.8% and by replacing the INOBS with, respectively: a 1:1 mixture of INOBS and tetraacetylethylenediamine; tetraacetylethylenediamine; or sodium nonanoyl oxybenzenesulfonate, at levels of from 1% to 5%, as the bleach activator ingredient. For additional bleach activators, see U.S. Pat. No. 4,412,934, Chung and Spadini, issued Nov. 1, 1983, incorporated by reference.

EXAMPLE XXI

A monophosphorus-built granular detergent composition containing bleach and bleach activator and relying on OEDBA for enhanced through-wash bleaching performance is as follows:

| Ingredient | Percent (wt.) |
|---|---|
| OEDBA | 0.4 |
| $C_{12.3}$ linear alkyl benzene sulfonate, sodium salt | 18.5 |
| $C_{14}$-$C_{15}$ alcohol sulfate, sodium salt | 10.3 |
| $C_{12-13}$ alcohol (6.5 ethoxylate) | 0.5 |
| palmitic/nonanoic acids 2.5:1 wt:wt | 0.46 |
| Zeolite A (1–10 micron) | 20.8 |
| Sodium carbonate | 26.9 |
| Sodium silicate, $Na_2O:SiO_2$ ratio = 1.6:1, dry basis | 1.8 |
| Sodium perborate monohydrate | 3.7 |
| INOBS* | 5.3 |
| Proteolytic enzyme (SAVINASE; 1.5 AU/g) | 0.6 |
| Silicone suds suppressor | 0.22 |
| Polyacrylate, sodium salt, av. m.w = 4,500 | 2.0 |
| $Na_2SO_4$ | 10.5 |
| Brightener, perfume | 0.5 |
| PEG 8000 | 0.4 |
| Minors (Perfume, brightener, unreacted LAB) | 1.0 |
| Water: Balance to: | 100.0 |

EXAMPLE XXII

A build granular detergent composition is as follows:

| Ingredient | Percent (wt.) |
|---|---|
| OEDBA (product of Example I, dry basis) | 0.7 |
| $C_{12}$-$C_{13}$ Linear alkylbenzene sulfonate | 5.7 |
| Tallow Alcohol Sulfate | 2.4 |
| $C_{14}$-$C_{15}$ alcohol (6 ethoxylate) | 5.0 |
| Carboxymethylcellulose | 0.3 |
| Sodium silicate, $Na_2O:SiO_2$ ratio = 1.6:1, dry basis | 8.0 |
| Maleate-co-methyl vinyl ether, m.w. avg. 60,000 | 1.8 |
| Proteolytic enzyme (SAVINASE; 4.0 KNPU/g) | 0.8 |
| Sodium sulfate | 19.0 |
| Sodium perborate, anhydrous basis | 8.6 |
| Magnesium sulfate | 0.4 |
| Sodium tripolyphosphate | 21.3 |
| Tallow Alcohol Ethoxylate (25) | 0.3 |
| Sodium carbonate | 7.0 |
| Water, perfume, brighteners, suds suppressor to: | 100.0 |

EXAMPLE XXIII

A built granular detergent composition is as follows:

| Ingredient | Percent (wt.) |
|---|---|
| OEDBA (product of Example V, dry basis) (as chelating agent/bleach performance enhancer) | 0.5 |
| $C_{12}$-$C_{13}$ Linear alkylbenzene sulfonate | 5.7 |
| Tallow Alcohol Sulfate | 2.5 |
| $C_{14-15}$ alcohol (6 ethoxylate) | 5.4 |
| Carboxymethylcellulose | 0.7 |
| Sodium silicate, $Na_2O:SiO_2$ ratio = 1.6:1, dry basis | 2.9 |
| Maleate-co-methyl vinyl ether, m.w. avg. 60,000 | 2.5 |
| PEG 4000 | 1.4 |
| Zeolite A (1–10 micron) | 20.5 |
| Proteolytic enzyme (SAVINASE; 4.0 KNPU/g) | 0.8 |
| Sodium sulfate | 19.0 |
| Tetraacetylethylene diamine (as bleach activator) | 2.5 |

-continued

| Ingredient | Percent (wt.) |
|---|---|
| Sodium perborate, anhydrous basis | 8.6 |
| Magnesium sulfate | 0.4 |
| Sodium tripolyphosphate | 21.3 |
| Tallow Alcohol Ethoxylate (25) | 0.3 |
| Sodium carbonate | 12.7 |
| Water, perfume, brighteners, suds suppressor to: | 100.0 |

As can be seen from the foregoing, OEDBA can be employed as a chelating agent or, regardless of the specific mode of action, as a useful cleaning ingredient in a variety of commercially useful cleaning products. Although the compositions herein are exemplified, in the main, by cleaning/bleaching compositions, the OEDBA material can also be used in any circumstance where a convenient, inexpensive chelating agent for metals such as iron and manganese or even toxic metals such as copper, is required. Thus, OEDBA can generally substitute the known chelant EDTA wherever it is used. Moreover, it is envisaged that OEDBA may be a useful sequestrant in a method for treating humans or animals to counteract toxic effects of ingestion of metal ions. In other alternate embodiments of the invention, OEDBA may be useful as a food stabilizer, low-level additive in dentifrice (both as a chelating agent and to help remove stains) or as a stabilizer for a non-bleaching peroxide in hair treatment cosmetics.

A simple method for sequestering transition metals is further illustrated by the following Example:

EXAMPLE XXIV

A solution of copper chloride (0.17 g, 1.00 millimole, dihydrate) in 10 ml. water is treated with OEDBA (0.39 g, 1.00 millimole, tetrasodium salt form). The color of the solution changes from pale blue to an intense blue, consistent with formation of a copper(II) chelate complex of OEDBA.

In a hair-care application, OEDBA can be used to provide a formulation termed a "neutralizer" for permanents:

| EXAMPLE XXV | |
|---|---|
| Ingredient | Percent (wt.) |
| OEDBA (product of Example V, dry basis) | 0.5 |
| Ditallowdimethylammonium chloride | 0.5 |
| Hydrogen peroxide | 1.9 |
| $C_{12-13}$ alcohol (6.5 ethoxylate) | 0.5 |
| Fragrance | 0.3 |
| Water Balance to: | 100.0 |

In another hair-care application, OEDBA can be used to provide a mild bleach for the hair:

| EXAMPLE XXVI | |
|---|---|
| Ingredient | Percent (wt.) |
| OEDBA | 0.6 |
| Hydrogen peroxide | 3.0 |
| $C_{12-13}$ alcohol (6.5 ethoxylate) | 0.3 |
| Fragrance | 0.3 |
| Water Balance to: | 100.0 |

A chlorine-free liquid laundry bleach is illustrated by the following:

EXAMPLE XXVI

| Ingredient | Percent (wt.) |
| --- | --- |
| OEDBA | 0.4 |
| Hydrogen peroxide | 3.0 |
| $C_{12-13}$ linear alkylbenzenesulfonic acid | 0.2 |
| $C_{12-13}$ alcohol (6.5 ethoxylate) | 0.8 |
| Fragrance | 0.3 |
| Water/$H_2SO_4$ pH correction to pH 2.5–3: | 100.0 |

EXAMPLE XXVII

A denture cleanser is prepared by admixing the ingredients shown below. When soiled dentures are soaked in an aqueous solution containing the admix, effective stain removal and whitening are obtained:

| Ingredient | Percent (wt.) |
| --- | --- |
| OEDBA | 5.0 |
| Mg(CPBA)$_2$* | 10.0 |
| Sodium bicarbonate | 30.0 |
| Sodium sulfate | 50.0 |
| Ultramarine blue dye | 0.01 |
| Water (hydrates) Balance to: | 100.0 |

*Magnesium bis(3-chloroperoxybenzoate) tetrahydrate: this illustrates a stable, solid-form magnesium peroxycarboxylate salt which can be used as an alternate bleach material in the practice of this invention, and which is disclosed in U.S. Pat. No. 4,483,781, Hartman, issued November 20, 1984, incorporated by reference.

High Performance Liquid Chromatography for OEDBA

In addition to the characteristic $^{13}C$ NMR spectra and Fast Atom Bombardment Mass Spectroscopic methods discussed hereinabove, High Performance Liquid Chromatography (HPLC) provides a useful and convenient approach to the detection of OEDBA. Any technique, is of course, subject to its known limitations.

High Performance Liquid Chromatography (HPLC) analyses herein for H$_4$(OEDBA), unreacted starting material (e.g., L-aspartic acid), and impurities or by-products (e.g., carboxymethylaspartic acid or its salts) are readily reproduced using the following conditions, by an analyst familiar with HPLC instrumentation:

Column: Rainin Microsorb C18-80-225 4.6 mm. I.D.×25 cm., new, equilibrated with mobile phase.

Mobile Phase: One gram of copper(II) acetate monohydrate (Aldrich) is placed in 800 ml. water and stirred for 1 hr. After filtering through 0.45 micron paper, the pale blue solution is treated with 10.0 ml. of 1.0M tetrabutylammonium hydroxide (Aldrich) in methanol, causing the formation of a blue precipitate. Concentrated phosphoric acid is added to dissolve the precipitate and to adjust the pH to 3.5. The resulting solution is transferred to a 2.0 L volumetric flask and is diluted to the mark with water. 400 ml. methanol is placed in a separate 2.0 L volumetric flask, and the copper ion solution is used to fill to the mark. The resulting methanolic copper ion solution is filtered through 0.45 micron paper. The filtrate constitutes the mobile phase.

HPLC Analysis is carried out using the above-identified column and the following additional equipment and conditions: Flow Rate: 1 ml./min.; Pump: A single Waters 510; Injector: Rheodyne 7125, injection volume 20 microliter; Detector: Lambda Max Model 481 LC Spectrophotometer, operating at a wavelength of 245 nanometers; Integrator: Waters 730 Data Module.

HPLC Sample Preparation: A known amount of either an OEDBA-containing material or of a standard, in the case of calibration, is weighed into a 10 ml. volumetric flask and a series of dilutions is carried out with mobile phase so as to give a peak area that falls within a conventionally made area/weight calibration plot. Typically, stock solutions of any sample to be analyzed have a concentration of about 2 mg./ml. in mobile phase and a further 50:1 dilution of stock in mobile phase is customary prior to injection.

Concentration Analysis: A calibration plot is made for direct correlation of peak areas to concentration expressed as weight per unit volume (mg./ml.). Thus, for a sample containing an unknown level of OEDBA, the calibration plot gives the concentration for an experimentally measured area. Knowing the dilution factor(s), the weight percent OEDBA in the sample can readily be determined. The weight percent OEDBA is calculated as weight percent H$_4$(OEDBA). This is considered for purposes herein and as defined above, to be the "active" level of OEDBA.

Standard Calibration Samples: A solution of H$_4$(OEDBA) (made by Method 2) is used as a reference material for calibration purposes. This solution is standardized on a weight basis by integration of its $^1H$ NMR using sodium benzoate as internal standard. The solution used for calibration is typically 17.8% H$_4$(OEDBA).

A solution of carboxymethylaspartic acid is used as a reference material for calibration purposes. This solution is standardized on a weight basis by integration of its $^1H$ NMR using sodium benzoate as internal standard. The solution used for calibration is typically 44% carboxymethylaspartic acid.

Solid L-aspartic acid (Aldrich, 98+%) is used as another reference material for calibration purposes.

Under the conditions described above, the [R,R'] and [S,S'] stereoisomers of OEDBA co-elute The [R,S'] and [S,R'] stereoisomers co-elute. The Method 1 synthesis, from L-aspartic acid, yields only the [S,S'] stereoisomer of OEDBA. The Method 1 synthesis, from D-aspartic acid, yields only the [R,R'] stereoisomer of OEDBA The Method 2 synthesis, from glycyl-L-aspartic acid, yields the [S,S'] and [S,R'] stereoisomers of OEDBA. The Method 2 synthesis, from glycyl-D-aspartic acid, yields the [R,R'] and [R,S'] stereoisomers of OEDBA. The Method 2 synthesis, from glycyl-D,L-aspartic acid, yields the [S,S'], [R,R'], 'S,R'] and [R,S'] stereoisomers of OEDBA. The convention used for designating absolute configuration is of labelling the first chiral center in any pair within braces [ ] as the chiral center attached to the amide nitrogen atom within the OEDBA structure.

Under the conditions described above, the various stereoisomers of OEDBA generally elute after L- aspartic acid and carboxymethylaspartate and prior to maleate and fumarate. Although it is well-known that retention times may vary, e.g., in function of the age of the column and variations in the precise composition of mobile phase, the OEDBA stereoisomers commonly elute at a retention time of the order of ten minutes, as two peaks about one minute apart.

What is claimed is:

1. A N,N'-(1-oxo-1,2-ethanediyl)-bis(aspartate) compound, or stereoisomer thereof, comprising an OEDBA moiety of the formula:

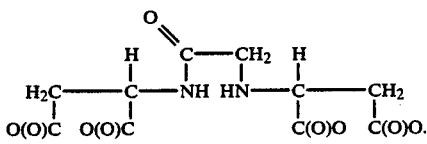

2. An OEDBA compound according to claim 1 having the formula

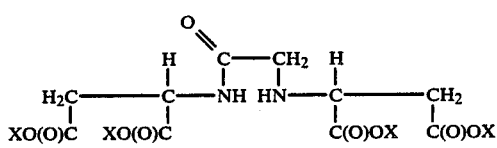

wherein each X is selected from the group consisting of H+, Na+, K+, Li+, $R_iN(H)_{4-i}{}^+$ and mixtures thereof; i is 0, 1, 2, 3 or 4 and when i is 1,2,3 or 4, R is a compatible hydrocarbyl residue such that the cation $R_iN(H)_{4-i}{}^+$ is water-dissociable.

3. A compound according to claim 2 having the formula $(R_iN(H)_{4-i}{}^+)_4(OEDBA)$ wherein i is 1,2,3 or 4 and R is selected from the group consisting of methyl, ethyl, propyl and butyl.

4. A compound according to claim 2 having the formula $X_4(OEDBA)$ wherein each X is selected from the group consisting of H+, Na+ and K+.

5. A chelating agent or sequestrant composition comprising an effective amount of a compound according to claim 4.

6. A detergency builder composition comprising an effective amount of a compound according to claim 4 and one or more other detergency builders.

7. A detergency builder composition according to claim 6 wherein all conventional detergency builder is in the form of nonphosphorus builder.

8. A composition according to claim 7 wherein the conventional detergency builder is selected from the group consisting of nitrogen-free polycarboxylate builders, zeolite builders, and mixtures thereof.

9. A detergent composition comprising a builder effective amount of an OEDBA compound according to claim 2 and a cleaning effective amount of a detersive surfactant.

10. A detergent composition according to claim 9 comprising from about 1% to about 50% by weight of said OEDBA compound.

11. A detergent composition according to claim 9 wherein said detersive surfactant is selected from the group consisting of anionic, nonionic, cationic and zwitterionic surfactants, or mixtures thereof.

12. A detergent composition according to claim 11 comprising from about 5% to about 30% by weight of said detersive surfactant.

13. A bleach composition comprising a bleach performance enhancing amount of an OEDBA compound according to claim 2 and a conventional bleaching agent.

14. A bleach composition according to claim 13, wherein said conventional bleaching agent is selected from the group consisting of perborate, persulfate, and percarbonate.

15. A bleach composition according to claim 13 comprising from about 0.05% to about 0.95% by weight of said OEDBA compound.

16. A process for preparing a compound according to claim 1, comprising reacting glycylaspartate and methyl maleate at alkaline pH in water followed by hydrolyzing the ester groups of the resulting OEDBA methyl ester.

17. A process for preparing a compound according to claim 1, comprising: reacting in an aqueous alkaline solution
(i) an amino acid with
(ii) a glyoxal reactant selected from glyoxal bisulfite, glyoxal/sodium bisulfite and glyoxal/sulfur dioxide; wherein said amino acid is aspartic acid or a water-soluble salt thereof and wherein during said reaction, the pH of said aqueous alkaline solution is maintained within the range from about 8 to about 9.

18. A process according to claim 17, wherein said pH is maintained by controlled sodium hydroxide addition, said process is carried out at a moderate temperature, and said aqueous alkaline solution is concentrated.

19. A method of sequestering metal cations in aqueous solution, comprising dissolving a sequestering effective amount of N,N'-(1-oxo-1,2-ethanediyl)-bis(aspartate) in a metal solution.

20. A method according to claim 19, wherein said N,N'-(1-oxo-1,2-ethanediyl)-bis(aspartate) has the form of the tetraprotic acid or sodium salt thereof.

* * * * *